United States Patent [19]

Pohlmann

[11] 4,204,535
[45] May 27, 1980

[54] LIGHTWEIGHT RESUSCITATOR ASSEMBLY

[76] Inventor: Charles Pohlmann, 621 N. Lima, Burbank, Calif. 91505

[21] Appl. No.: 859,277

[22] Filed: Dec. 12, 1977

[51] Int. Cl.² .......................................... A61M 16/00
[52] U.S. Cl. ........................... 128/202.13; 128/204.26
[58] Field of Search ............... 128/145.8, 145.6, 145.7, 128/145.5, 140 R, 142 R, 142.2, 147, 172, 185, 188, 203, 205, 214 R; 248/311.3, 125, 127, 161, 159, 165, 166, 150; 211/74 R; 5/317 R

[56] References Cited

U.S. PATENT DOCUMENTS

| | | | |
|---|---|---|---|
| 2,138,988 | 12/1938 | Thomas | 137/606 X |
| 2,257,249 | 9/1941 | Thomas | 137/606 X |
| 2,324,389 | 7/1943 | Heidbrink | 128/203 X |
| 2,382,610 | 8/1945 | Dann | 128/145.8 |
| 2,408,136 | 9/1946 | Fox | 128/145.8 |
| 2,957,187 | 10/1960 | Raia | 248/311.3 X |
| 3,235,038 | 2/1966 | Nesslinger | 248/166 X |
| 3,598,117 | 8/1971 | Cearly | 128/145.8 |
| 4,060,079 | 11/1977 | Reinhold, Jr. | 128/145.8 |

FOREIGN PATENT DOCUMENTS

| | | | |
|---|---|---|---|
| 231281 | 1/1964 | Austria. | |
| 1566508 | 11/1970 | Fed. Rep. of Germany | 128/203 |
| 505088 | 12/1954 | Italy | 128/145.8 |

*Primary Examiner*—Henry J. Recla
*Attorney, Agent, or Firm*—John E. Wagner

[57] ABSTRACT

A compact lightweight resuscitator system for use by paramedics and rescue personnel is described. The basic apparatus, including a full cylinder of oxygen, weighs about fourteen pounds. It comprises a single channel aluminum frame on which is fastened an oxygen cylinder, a regulator and low pressure manifold, a demand valve with three sizes of resuscitator masks, a regulated and indicated flow inhalation circuit, a set of airways, and a variable rate aspirator with hose and catheter. Additional accessories, which bring the weight to sixteen pounds, include a humidifier for the inhalation circuit, another line and coupler for attaching a second oxygen cylinder and an IV stand. The resultant system enables all standard procedures to be used by paramedic personnel and rescue technicians but is greatly reduced in size and weight.

6 Claims, 5 Drawing Figures

FIG. 1
FIG. 2
FIG. 3
FIG. 5
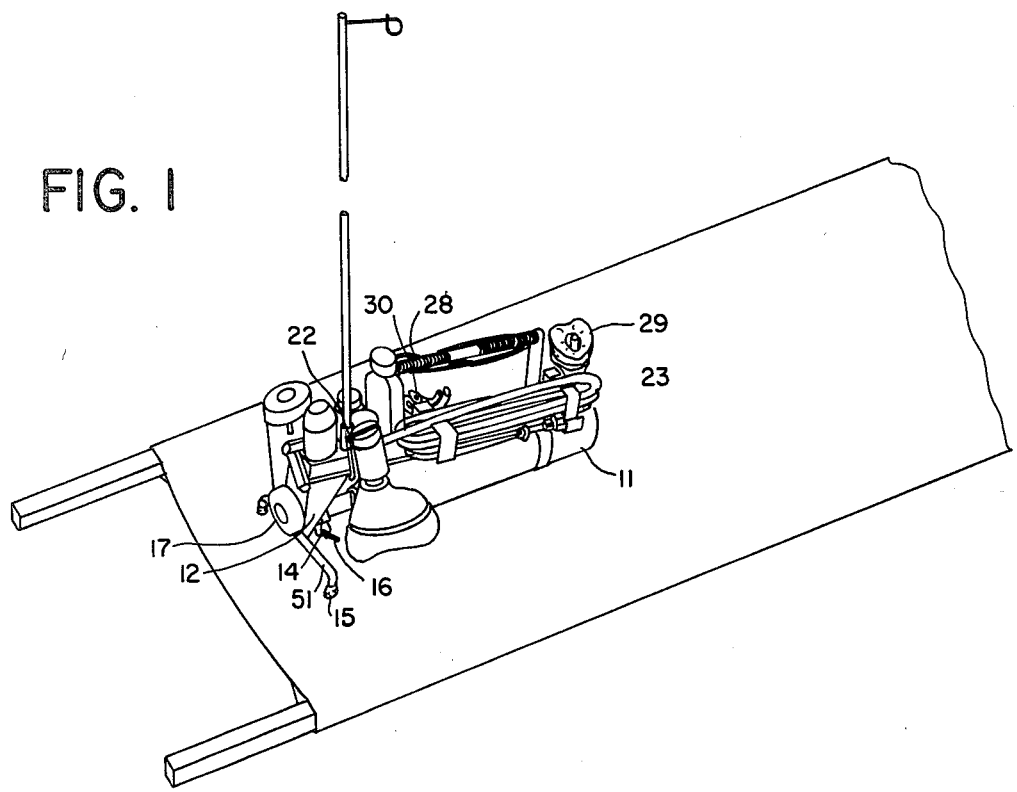
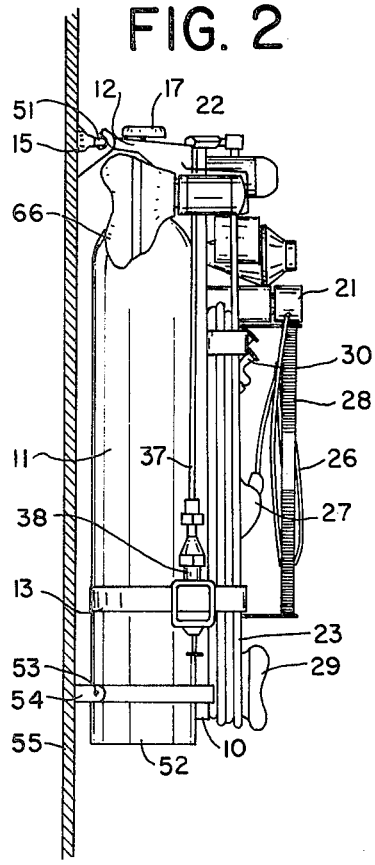
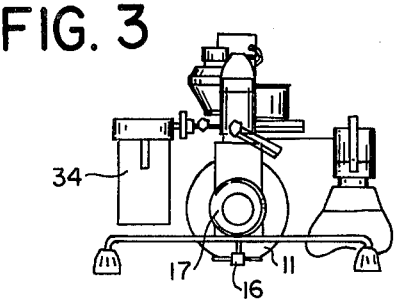
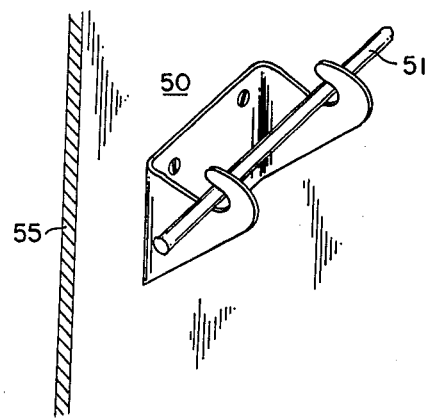

LIGHTWEIGHT RESUSCITATOR ASSEMBLY

BACKGROUND OF THE INVENTION

This inventive apparatus is a lightweight resuscitation system usable by rescue personnel.

A standard resuscitation system carried by rescue personnel usually contains two bottles of pressurized oxygen, a high pressure regulator, a low pressure manifold, a demand valve with respirator mask, an aspirator, an IV stand, and other ancillary devices. This unit usually weights more than forty pounds, is not convenient to carry, and is bulky in operation. However, until several years ago, this weight and size could be accommodated.

More recently, because of advances in rescue techniques and equipment, the rescue technician now is required to carry a greater variety of equipment. Thus, a smaller and lighter but complete resuscitator system has become necessary.

SUMMARY OF THE INVENTION

This inventive resuscitator system is based on a single frame member which is strapped along the top of the oxygen cylinder, and projects over and across the valve end. To this frame is connected all of the ancillary equipment necessary to complete the resuscitator system as enumerated above. The frame is adapted to operate with a D or E size oxygen cylinder, and has an additional reserve cylinder connector so that uninterrupted service from a sequence of oxygen cylinders can be provided.

A carrying handle is provided with two grips, so that the load can be carried at its center of gravity with either a D or E size cylinder connected.

All of the functional components are bolted directly to the frame which is made of aluminum, as are the brackets and straps. The handle is plastic. The system, with a complete set of accessories, weighs sixteen pounds, and is compact enough to be carried by hand, or easily on the stretcher between the patient's legs.

The object of this invention, then, is to provide a complete resuscitation system which is compact and light in weight.

BRIEF DESCRIPTION OF THE DRAWINGS

FIG. 1 shows the system in place on a stretcher;

FIG. 2 is a side view of the unit;

FIG. 3 is an end view of the unit;

FIG. 5 is a perspective view of the mounting bracket.

DETAILED DESCRIPTION OF THE INVENTION

Figure 4:
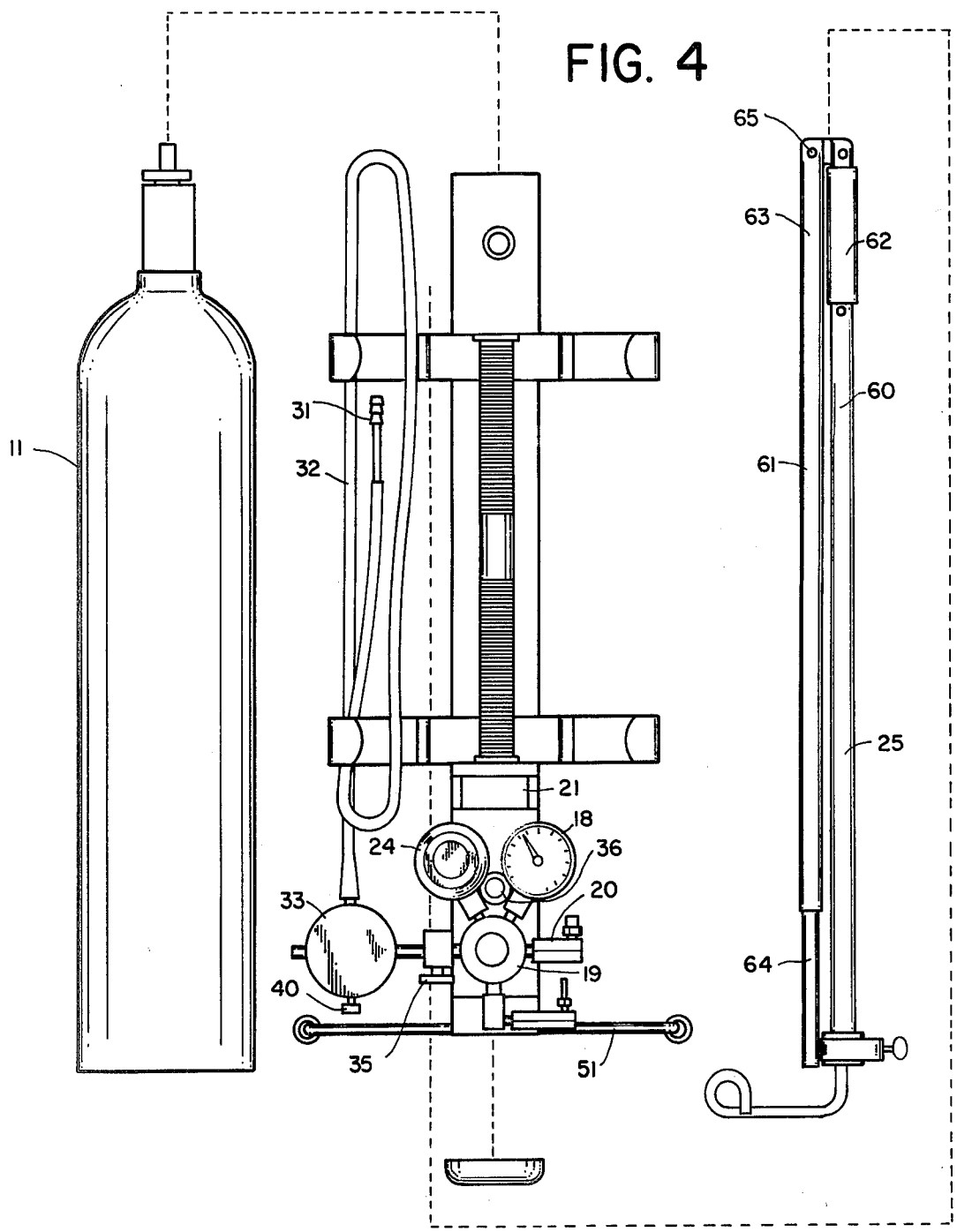
FIG. 4 is an exploded view showing how the meters, manifold, oxygen cylinder and IV stand mount onto the frame.

As shown in FIGS. 1, 2 and 4, the basic frame of the apparatus is provided by a channel or frame 10 which is connected along the top of the oxygen cylinder 11. This channel is "C" shaped in cross section, with the open side toward the cylinder. The frame is provided with an extension 12 which projects across the end of the oxygen cylinder, ending in an attachment point for a rod 51 and two feet 15. The oxygen cylinder 11 is maintained in position against the frame by means of a metal strap 13 and a locking coupler 14 of FIG. 1. The coupler 14 appearing in FIG. 1 contains a threaded hole for a screw 16 which, when tightened, forces the oxygen bottle orifice upward into sealed engagement with a line connecting the oxygen cylinder to the regulator 19. After this connection is made, a valve wrench 17 is attached onto the cylinder valve stem and may be rotated to initiate oxygen flow to the regulator and manifold.

The oxygen, at high pressure, first goes to the regulator 19 and pressure gauge 18 of FIG. 4, and is then reduced to a low pressure of 50 PSI by the regulator 19. It then is supplied to the manifold 20 which is a plurality of lines supplying oxygen to the remainder of the system.

This low pressure oxygen is supplied to the demand valve 22 through line 23, seen most clearly in FIG. 2.

An adult mask 66 is normally attached to the demand valve 22. Infant's and child's masks 29 are normally stored to the rear of the handle 28.

Oxygen is also supplied through metering valve 24 of FIG. 4, and through a humidifier 21 and hose 26 of FIG. 2 to an inhalation mask 27. The metering valve 24 normally varies the flow of oxygen from 1 to 15 liters per minute. This flow is directed into the bottom of the humidifier 21 which is a plastic bottle filled with water, preferably distilled water. The humidified oxygen is taken from the upper portion of the humidifier and is then coupled to the inhalation mask 27 which is normally stored beneath the handle 28 when not in use.

Airways 30 of FIG. 1 are stored below the handle, and are kept in place by means of a coil spring loop attached to the frame.

An aspirator catheter 31 of FIG. 4 is connected by hose 32 to an aspirator reservoir 34 of FIG. 3 and venturi suction mechanism 33. Oxygen at 50 PSI is forced through a venturi to produce a vacuum which is felt internally in the reservoir 34. The amount of vacuum is adjustable by valve 35 which is set to produce the vacuum required.

Button 40 is pushed to provide a momentary suction. The button can be locked down, providing a continuous suction. An IV stand 25 is stored alongside the frame, as shown in FIG. 4, and is adapted to mount into fitting 36 of FIG. 4 when in use. The stand is adjustable in height.

The stand comprises a bottom 60 and a top 61. To use this stand, the narrow bottom section 64 is inserted into fitting 36. The top 60 is then raised to the point where both parts are in line allowing the sleeve 62 to drop into contact with stop 63. Since the distance from the stop 63 to the swivel point 65 is approximately one half the sleeve length, the sleeve, after dropping, overlaps both parts, locking them into alignment.

The system is supplied with an additional hose 37 and coupler 38 in FIG. 2 to allow a reserve cylinder to be attached. To provide for continuous service without interruption, as the primary cylinder becomes empty, a second cylinder is connected in parallel to the first. The primary cylinder valve remains open to partially charge up the primary cylinder. Next, the primary cylinder valve is shut off, and the secondary supply of oxygen is used. Then, the primary cylinder is reactivated while a fresh secondary cylinder is installed, completing the cycle. A check valve is supplied between the primary and secondary cylinders so that flow will be in one direction, from secondary to primary cylinders only via the regulator. A shock check is also provided at the secondary cylinder inlet to prevent a blast of oxygen from being felt in the system when a fresh reserve cylinder is installed. This shock check is a small orifice in the line that limits flow from the reserve cylinder to a predetermined limit.

Even if one cylinder is used without employing the reserve cylinder circuit, the time that the system must be out of service for changing cylinders is minimal. The procedure to replace cylinders is to remove valve wrench 17 of FIG. 1, and loosen screw 16 of coupler 14. The assembly can then be removed from the cylinder with a simple upward lift. This process is reversed to install a fresh cylinder.

This resuscitator assembly can be wall mounted for storage and use in a hospital room or in a moving vehicle. For this purpose, a bracket 50 of FIG. 5 is mounted on the room or vehicle wall and the unit is suspended in this bracket by means of the rod 51 connecting the feet 15. In the stowed position, the distance between the rod 51 and the wall is equal to the distance from the rod 51 to the feet 15, and because the bracket 50 curls over the rod 51, the resuscitator assembly cannot be lifted up out of the bracket unless the bottom of the assembly is first lifted away from the wall. The bottom of the unit is attached to the wall by means of a looped bracket member 52 of FIG. 2 which rotates about point 53 of a bracket 54 permanently attached to the wall 55. The result is that the resuscitator assembly is usable in the stored position, and will not fall from the wall, even in a vehicle roll-over.

As is shown most clearly in FIG. 4, the pressure gauge 18, manifold 20, inhalator metering valve 24, venturi mechanism 33 and valve 35 are all centrally located on the assembly. This results in a decreased liklihood of breakage of the equipment, with its resultant rapid loss of oxygen.

The assembly is designed so that the aspirator venturi mechanism 33 can be removed rapidly to accommodate a second demand valve. Each demand valve automatically supplies oxygen at low pressure to the mask. To the extent that this second demand valve is in series with the venturi needle valve, the flow to this second demand valve can be manually and adjustably limited. This is useful when treating infants where a limited flow and lower pressure may be desirable.

The above described embodiments of this invention are merely descriptive of its principles and are not to be considered limiting. The scope of this invention instead shall be determined from the scope of the following claims, including their equivalents.

What is claimed is:

1. A resuscitator assembly comprising:
   an oxygen cylinder of a first or second size;
   a frame member fastenable to said cylinder, said member extending along a substantial portion of the length of said cylinder;
   fastening means securing said frame to said cylinder;
   a regulator mounted on said frame and coupled to said oxygen cylinder for accepting high pressure oxygen from said cylinder and for providing a regulated supply of pressure oxygen;
   a high pressure gauge mounted on and communicating with the high pressure side of said regulator to show the cylinder internal pressure;
   a respirator and flow control valve therefor;
   hose means coupling said flow control valve to the low pressure side of said regulator;
   a venturi chamber including a partial vacuum outlet connected to said regulator and driven by the regulated oxygen supply for producing a partial vacuum;
   aspirator means coupled to the partial vacuum outlet of said venturi chamber;
   means storing on said frame said respirator and demand valves, aspirator means and interconnecting hoses therefor; and
   further comprising an elongated handle attached to and extending along said frame, said handle being long enough to extend over the two center of gravity produced by either size of oxygen cylinder to provide a convenient carrying point for the resuscitator assembly when equipped with either size cylinder.

2. The apparatus of claim 1 further comprising coupling means for an additional hose and oxygen cylinder connected to said regulator.

3. The apparatus of claim 2 wherein said coupling means for an additional hose to be connected to said regulator includes a check valve to prevent oxygen from entering said additional oxygen cylinder.

4. The apparatus of claim 3 wherein said frame incudes a recepticle in the upper side thereof;
   an IV stand adapted to mount on said frame in said receptacle, and said IV stand being foldable and adapted to be stored folded, when not in use, alongside said frame.

5. The combination in accordance with claim 1 including an inverted "U" shaped member secured to said frame transverse to the length of said frame wherein the ends of said "U" shaped member comprises feet which with the cylinder, provide three point support for the apparatus.

6. The apparatus of claim 5 further comprising means for releasably attaching said apparatus to a wall;
   said means including a bracket adapted to be secured to a wall and having a pair of reentrant hook arms extending outward from such wall;
   said hook arms engagable with said "U" shaped member of spaced points to support said apparatus.

* * * * *